United States Patent [19]

Grew et al.

[11] 4,140,687
[45] Feb. 20, 1979

[54] PROCESS FOR THE PREPARATION OF 8-HALODIHYDROCODEINONE HYDROHALIDES AND CODEINE

[75] Inventors: Edward L. Grew, Huntingdon, England; Henry A. S. Payne, Linlithgow, Scotland

[73] Assignee: MacFarian Smith Limited, Edinburgh, Scotland

[21] Appl. No.: 821,834

[22] Filed: Aug. 4, 1977

[30] Foreign Application Priority Data

Aug. 17, 1976 [GB] United Kingdom ............... 34195/76

[51] Int. Cl.² .................. C07D 489/02; C07D 489/00
[52] U.S. Cl. ......................................... 546/45; 546/46
[58] Field of Search ......................................... 260/285

[56] References Cited

U.S. PATENT DOCUMENTS

| 2,778,832 | 1/1957 | Gates | 260/285 |
| 3,112,323 | 11/1963 | Krausz | 260/285 |
| 4,052,402 | 10/1977 | Calvo | 260/285 |
| 4,054,566 | 10/1977 | Rapoport et al. | 260/285 |

FOREIGN PATENT DOCUMENTS

| 839732 | 7/1976 | Belgium. |
| 937128 | 9/1963 | United Kingdom. |
| 1472397 | 5/1977 | United Kingdom. |

OTHER PUBLICATIONS

Gavard et al., Bull Soc. Chim France, 1965, No. 2, pp. 486–490.
Barber et al., J Med. Chem., vol. 19, No. 10, pp. 1175-1180, 10/76.

Primary Examiner—Paul M. Coughlan, Jr.
Assistant Examiner—Diana G. Rivers
Attorney, Agent, or Firm—Bacon & Thomas

[57] ABSTRACT

Compounds of the general formula

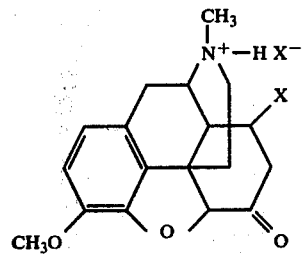

(III)

in which X represents halogen.

These compounds are useful in the production of codeinone and codeine substantially free from impurities.

26 Claims, No Drawings

PROCESS FOR THE PREPARATION OF 8-HALODIHYDROCODEINONE HYDROHALIDES AND CODEINE

This invention relates to novel derivatives of dihydrocodeinone, to processes for their production and to their use in the production of codeinone and codeine.

It is known from British Pat. No. 937,128 that thebaine may be converted to codeinone by a process which comprises reacting thebaine or a salt thereof with a hydrohalic acid in an anhydrous organic medium and treating the resulting reaction product with an amount of a basic agent, preferably in an aqueous medium as defined in that specification, such as to secure a pH of the range 8 - 12 for the final reaction mixture.

The anhydrous nature of the first stage of the process of the patent is emphasized, and it will be appreciated that a process which depends upon keeping the reaction medium free of water can be economically unattractive. The organic media specified in the patent specification e.g. ethers, chlorinated hydrocarbons, aromatic hydrocarbons, esters etc. are specifically referred to as "diluents", and apparently function pure as inert reaction vehicles; it is not suggested that they take part in the reaction between thebaine and the hydrohalic acid.

The organic media mentioned do not include carboxylic acids such as glacial acetic acid or enolizable carbonyl compounds, or indeed any other of the compounds hereinafter defined as reactive compounds.

The above mentioned specification suggests, when discussing a possible theoretical explanation for the process disclosed therein, that there is formed, as intermediate in the process, the 6-halocodeine methyl ether of the formula:

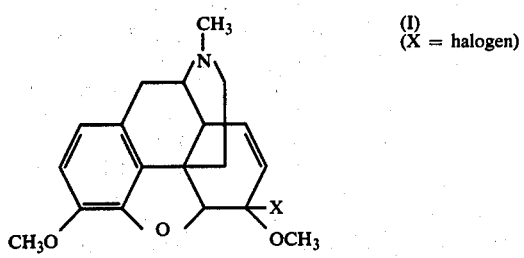

(I) (X = halogen)

In a later investigation of the process reported by Gavard et al in a paper in Bull. Soc. Chim. France. 1965, No. 2, 486–490, it was shown fairly conclusively that the intermediate formed is not I but a 6,8-dibromotetrahydrothebaine of the formula:

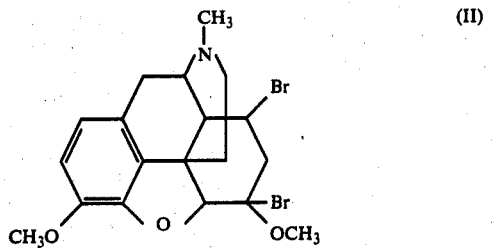

(II)

We have now found that if the reaction between thebaine and a hydrohalic acid is carried out in the presence of certain reactive compounds (as hereinafter specified), which may, in certain cases, also serve as the reaction solvent, a different reaction takes place leading to the production under acid conditions of novel intermediates which are 8-halodihydrocodeinone hydrohalides of the formula

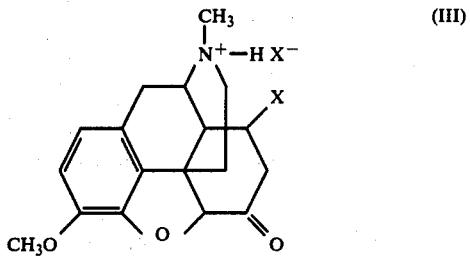

(III)

where X is halogen, e.g. bromine, chlorine or iodine preferably bromine or chlorine.

Particularly preferred intermediates of formula III are 8-bromodihydrocodeinone hydrobromide, and 8-chlorodihydrocodeinone hydrochloride.

The novel intermediates of formula III have the advantage that they readily separate out from the reaction mixture, in a relatively pure and frequently crystalline form, and can thereby be used to make both codeinone and codeine substantially free from impurities. The importance of a process which allows the manufacture of pharmaceutical grade codeine from relatively pure intermediates will be appreciated, particularly in view of the fact that the reaction of thebaine and a hydrohalic acid normally gives rise to a complex reaction mixture containing undesirable by-products.

Surprisingly, the intermediates of formula III can be formed under non-anhydrous conditions, for example in the presence of up to 10% of water based on the overall volume of the reaction mixture.

A further advantage of our new process is that it may be carried out with good yield at reaction temperatures readily achievable under manufacturing conditions, for example a temperature between 10° C., and ambient temperature.

The reactive compound is selected from one of the following:

(1) A lower e.g. $C_{1-6}$ aliphatic carboxylic acid, for example:
   (a) a $C_{1-6}$ alkanoic acid including formic acid, but preferably acetic or propionic acid
   (b) a substituted aliphatic carboxylic acid, such as a halo, hydroxy or oxo substituted acid; for example a $C_{1-6}$ halo, hydroxy or oxo substituted alkanoic acid e.g. chloroacetic, trifluoroacetic, lactic or pyruvic acid
   (c) a polybasic, such as dibasic, carboxylic acid, e.g. oxalic acid, (2) An enolizable carbonyl group-containing compound for example:
   (a) a lower aliphatic aldehyde, such as a $C_{2-6}$ alkanal e.g. acetaldehyde
   (b) a lower aliphatic ketone, such as a $C_{3-12}$ alkanone e.g. acetone, methyl ethyl ketone, methyl isopropyl ketone or diisopropylketone
   (c) a cyclic ketone, e.g. cyclopentanone or cyclohexanone
   (d) a diketone, such as a $C_{4-12}$ alkanedione e.g. butane-2,3-dione
   (e) a mixed aliphatic aromatic ketone, e.g. acetophenone or an aliphatic araliphatic ketone, e.g. methyl benzyl ketone
   (f) a keto ester, e.g. ethyl acetoacetate (3) chloral hydrate (4) Water, preferably in small quantity for example 1-5 moles, advantageously 1-2 moles, per mole of thebaine and preferably in conjunction with an inert solvent as indicated below. The water may be generated in situ.

(5) An aromatic aldehyde, such as benzaldehyde.

(6) An aromatic ketone, such as benzophenone.

By the term "enolizable" we mean that the compound has an α-hydrogen atom relative to the carbonyl group.

Mixtures of these reactive compounds may be used, for example aqueous acetic acid or an acetic acid/acetone mixture.

The reactive compound may be used in admixture with an inert solvent or may in suitable cases also serve as the total solvent for the reaction.

Inert solvents which may be used in the process of the present invention in combination with the reactive compounds include halogenated hydrocarbons, in particular chloroform; ethers, for example diisopropylether, 1,2-dimethoxyethane and bis(2-methoxyethyl) ether (diglyme); and cyclic ethers, for example dioxan.

Both water-miscible ethers such as dioxan and water-immiscible ethers such as di-n-butyl ether may be used as inert solvent in conjunction with a small quantity of water as the, or one of the, reactive compounds.

Reaction may be effected with the reactive compound at a temperature in the range −20° to +80° C., preferably +5° to +25° C.

The hydrogen halide may be introduced as a gas or in solution in a suitable solvent or may be generated in situ by the action of a suitable acid, for example p-toluene sulphonic acid or oxalic acid, on a suitable halide salt. Salts which may be used include alkali metal chlorides, bromides and iodides, ammonium halides and quaternary ammonium halides. The reaction may be carried out in a suitable solvent such as acetone at a temperature in the range +15° to 60° C.

Intermediates of formula III are readily converted, on the addition of a base, under both aqueous and anhydrous conditions, to codeinone which may be reduced to codeine by established procedures, e.g. treatment with sodium borohydride in methanol or ethanol, or by a Meerwein-Pondorf-Verley reduction with metal alcoholates such as aluminium isopropoxide in isopropanol.

It has also been found, and this is a preferred embodiment of our invention, that the conversion of the intermediates of formula III to codeine may be effected in a single step by the action of a base, preferably a strong base, together with a reducing agent, or alternatively by means of a reagent with basic properties capable of reducing a carbonyl group. Such reagents include metal alcoholates, such as aluminium and magnesium alkoxides e.g. aluminium isopropoxide.

The invention therefore provides a new and simple process for the conversion of thebaine to codeine which comprises treating thebaine with a hydrohalic acid, preferably hydrogen bromide, in the presence of one of the reactive compounds specified above and subsequently treating the product with either:

(A) a mixture of a base and a reducing agent, for example a mixture of sodium borohydride and sodium hydroxide conveniently in an alkanol such as methanol, or (B) a reagent with basic properties capable of reducing a carbonyl group, for example aluminum isopropoxide.

A wide range of reaction solvents may be used in the conversion of the intermediates III to either codeinone or directly to codeine. Suitable solvents can be found in both the reactive compounds and inert solvents illustrated above. We prefer to use aqueous solvents such as aqueous alcohols, for example aqueous methanol.

A wide range of bases may be used for converting the intermediates of formula III to codeinone. As mentioned above such bases may be capable of reducing a carbonyl group so that codeine is obtained directly. As an alternative, reduction may be effected simultaneously with the conversion using the base, by the use of a reducing agent, or a reducing agent may be used subsequently. Such bases include (a) an alkali metal hydroxide, preferably sodium or potassium hydroxide (b) an alkaline earth metal hydroxide, for example barium hydroxide (c) an alkali metal bicarbonate or carbonate, for example sodium carbonate or sodium bicarbonate (d) an aluminum alkoxide for example aluminum isopropoxide (e) an alkali metal alkoxide, such as sodium methoxide or ethoxide (f) an alkaline earth metal alkoxide (g) primary amines $RNH_2$ where R is an optionally substituted alkyl group (h) secondary amines $R'R''NH$, where R' and R'' are the same or different and each represents an optionally substituted alkyl group or together with the nitrogen atom form a heterocyclic ring e.g. piperidine.

(i) tertiary amines of formula $R'R''R'''N$ where R', R'' and R''' are the same or different and each represents an optionally substituted alkyl group or two of such groups together with the nitrogen atom form a heterocyclic ring.

(j) quaternary ammonium hydroxides such as tetraalkyl ammonium hydroxides, e.g. tetramethyl ammonium hydroxide (k) ammonia or ammonium hydroxide (l) an alkylene oxide such as propylene oxide.

The conditions under which the bases are used will be determined by the nature of the base and thus for example bases (d), (e) and (f) should be used under anhydrous conditions. Reaction with base may be effected at a temperature in the range −20° to +50° C., preferably +5° to +25° C.

Suitable reducing agents for the reduction to codeinone, either subsequently or simultaneously with the treatment with the strong base, include sodium or potassium borohydride, sodium cyanoborohydride and lithium aluminum hydride, of which the borohydrides are preferred.

The choice of solvent must be one which is compatible with the reducing agent to be used since some solvents are not suitable to use with certain reducing agents, such as ketones with sodium borohydride.

In a representative procedure 8-bromodihydrocodeinone hydrobromide is converted in one step directly to codeine in good yield by treatment with a mixture of sodium hydroxide and sodium borohydride in aqueous methanol at room temperature as exemplified below. This procedure provides the possibility of a simple one stage conversion of thebaine directly to codeine. Thus if thebaine is treated with hydrogen bromide in glacial acetic acid and the reaction mixture is added to sodium hydroxide and sodium borohydride in aqueous methanol, codeine is the main product formed.

The following Examples illustrate the invention.

EXAMPLE 1

8-Bromodihydrocodeinone hydrobromide

A 45% w/v solution of anhydrous hydrogen bromide in glacial acetic acid (6 ml ≡ 2.7 g HBr) was diluted with glacial acetic acid (3 ml) and added dropwise with stirring to a chilled (iced water bath) solution of thebaine (2 g) in glacial acetic acid (10 ml). The addition took place over a period of 10 minutes during which time a solid separated. Stirring was continued for a further forty minutes, the temperature of the reaction mixture being allowed to rise to ambient during this period. The solid was then filtered off, washed with anhydrous ether and dried in vacuo at 30° C. A second crop was obtained by chilling the mother liquors. The combined weight of the two crops of 8-bromodihydro-codeinone hydrobromide obtained was 1.67 g, melting point 197°–200° C., NMR : 3.06 $\tau$, 3.18 $\tau$ (2 arom H, C-1, C-2), 4.76 $\tau$ (1H, C-5), 5.75 $\tau$ (1H, C-8), 6.17 $\tau$ (-OCH$_3$, C-3), 7.46 $\tau$ (-N-CH$_3$). IR (KBr disc) 2597 cm$^{-1}$: quaternary N-H; 1727 cm$^{-1}$: non-conjugated 6 ring ketone.

EXAMPLE 2

8-Bromodihydrocodeinone hydrobromide

A solution of anhydrous hydrogen bromide (2.45 g) in 100% formic acid (6 ml) was added dropwise with stirring to a cooled (−10° C.) solution of thebaine (2 g) in chloroform (6 ml) over a period of 10 minutes. After five minutes the cooling bath was removed and after a further five minutes anhydrous ether (5 ml) was added dropwise to the mixture over 15 minutes. A crystalline solid precipitated. Stirring was continued for one hour and 20 minutes at room temperature. The solid was collected, washed with a mixture of anhydrous ether (7 ml) and formic acid (3 ml) and dried in vacuo to give the title compound (0.96 g), m.p. 185°–188° C., with an infra red spectrum identical with that of the product of Example 1.

EXAMPLE 3

8-Bromodihydrocodeinone hydrobromide

A solution of hydrogen bromide (2.3 g) in propionic acid (6 ml) was added dropwise with stirring to a cooled (−20° C.) solution of thebaine (2.0 g) in chloroform (6 ml) over a period of 6 minutes. The cooling bath was removed and stirring continued for 1¾ hours. During this time a crystalline solid separated. This solid was filtered off, washed with a mixture of anhydrous ether (7 ml) and propionic acid (3 ml) and dried in vacuo to give the title compound (1.2g), m.p. 181°–183° C., with an IR spectrum identical with that of the product of Example 1.

EXAMPLE 4

8-Bromodihydrocodeinone hydrobromide

A solution of thebaine (3.11 g) in dry chloroform (50 ml) was treated with chloroacetic acid (1.89 g). The resultant mixture was cooled in an ice-bath and anhydrous hydrogen bromide gas (3.66 g) was bubbled into the flask with stirring over 18 minutes. AFter 1½ hours di-isopropyl ether (1 ml) was added dropwise and the cooling bath was removed. Some fifteen minutes later, a fine precipitate began to separate. After stirring for a further hour, the product was filtered off, washed with chloroform and dried in vacuo to give the title compound (3.29 g) m.p. 178°–180° C. The structure was confirmed by IR spectroscopy.

EXAMPLE 5

8-Bromodihydrocodeinone hydrobromide

A solution of thebaine (3.11 g) and trifluoroacetic acid (2.4 g) in dry chloroform (35 ml) was cooled to 3° C. in an ice-bath and dry hydrogen bromide (3.68 g) bubbled in with vigorous stirring over a period of 14 minutes. One hour and five minutes later the cooling bath was removed and the temperature allowed to rise to room temperature. Some 50 minutes later a cloudiness developed and some red gum began to separate. Four hours later, dry methanol (10 ml) was added and a buff solid rapidly separated from the mixture. After a further 40 minutes the solid was collected, washed with chloroform and dried under vacuum to give the title compound (1.62 g), m.p. 183°–185° C. The structure was confirmed by IR spectrum, TLC and melting point.

EXAMPLE 6

8-Bromodihydrocodeinone hydrobromide

Thebaine (3.11 g) was stirred in diglyme (15 ml) and the slurry cooled to below 5° C. using an ice water bath. A 45% w/v solution of hydrogen bromide in acetic acid (5.4 ml, 3 equivalents) was then added dropwise over 5 minutes. After approximately 30 minutes a fine solid began to separate. Stirring was maintained for a further 15 minutes and the solid was then filtered off, washed with cold diglyme (2 × 3 ml) and dried under vacuum at 30° C. to give the title compound (1.56 g), m.p. 184°–186° C.

EXAMPLE 7

8-Bromodihydrocodeinone hydrobromide

A cold (0° C.) suspension of thebaine (2 g) in dimethoxyethane (12 ml) was treated dropwise with stirring with anhydrous hydrogen bromide (2.0 g) in acetic acid (5 ml) over a period of 14 minutes. The suspended thebaine dissolved to give a dark red solution. Solid began to separate after 20 minutes. Stirring was continued for a further 45 minutes when the solid was collected, washed and dried in vacuo.

A second crop separated from the mother liquors on standing and was also collected. The two crops were combined to give the title compound (2.14 g)

EXAMPLE 8

8-Bromodihydrocodeinone hydrobromide

A solution of thebaine (2 g) in 90% v/v aqueous acetic acid (7 ml) was chilled (iced water bath) and treated dropwise with stirring with 40% hydrogen bromide in acetic acid (6 ml) over a period of 13 minutes. The solution became dark red in colour. The cooling bath was removed when the addition was complete and the temperature allowed to rise. After 15 minutes crystals separated. Stirring was continued for a further 1 hour and 20 minutes when the solid was filtered off, washed and dried in vacuo to give the title compound (940 mg), characterised by infra red spectrum and melting point

EXAMPLE 9

8-Bromodihydrocodeinone hydrobromide

A mixture of water (360 mg) and dioxan (5 ml) was added to a suspension of thebaine (3.11 g) in dry dioxan (35 ml). The flask was cooled in an ice/water-bath and hydrogen bromide gas (4.85 g) was bubbled in with stirring over a period of 5 minutes. After the first minute of bubbling almost all the thebaine had dissolved. Solid began to precipitate just before the bubbling was completed. The cold bath was removed. Stirring was continued for 1 hour 25 minutes before filtering the product, washing with ice-cold methanol and drying in vacuo to give the title compound (2.78 g), m.p. 185°–186° C.

EXAMPLE 10

8-Bromodihydrocodeinone hydrobromide

Chloroform (15 ml) was distilled off from a solution of thebaine (3.11 g) in chloroform (50 ml). Water (360 mg) was then added and the solution cooled to −30° C. The water solidified. A solution of anhydrous hydrogen bromide in di-n-butyl ether (12.2 ml containing 4.86 g HBr) was added to thebaine solution with vigorous stirring. After 30 minutes, a fine precipitate of 8-bromodihydrocodeinone hydrobromide began to separate. Stirring was continued for 1½ hours, the temperature being allowed to rise slowly. The product was filtered off, washed with chloroform and a small volume of methanol and dried to give the title compound (3.65 g) as a colourless solid, m.p. 187°–189° C.

EXAMPLE 11

8-Bromodihydrocodeinone hydrobromide

Anhydrous hydrogen bromide (17.6 g) was bubbled into dry di-n-butyl ether (30 ml) at −25° C. Thebaine (3.89 g) suspended in dry acetone (40 ml) at room temperature was treated slowly with stirring with a portion of the hydrogen bromide solution (9 ml i.e. ca 5.25 g HBr). The suspended solid dissolved up rapidly to give an orange-yellow solution. Less than a minute later solid began to precipitate. Stirring was continued for a further 33 minutes when the solid was filtered off, washed with chilled acetone (2 × 5 ml) and dried in a vacuum oven to give the title compound (3.77 g), identified by its IR spectrum and melting point (195°–197° C. (dec.)).

EXAMPLE 12

8-Bromodihydrocodeinone hydrobromide

Thebaine (3.11 g) suspended in cyclopentanone (20 ml) was chilled (−10° C.) and treated with a solution of anhydrous hydrogen bromide (4.86 g) in dry diisopropyl ether (8.5 ml) with vigorous magnetic stirring. The cooling bath was removed and after 17 minutes a fine precipitate began to separate. Stirring was continued for a further hour when the solid was collected, washed with a small volume of methanol and dried in vacuo to give the title compound (2.92 g), m.p. 203°–204° C.; the structure was confirmed by IR spectroscopy.

EXAMPLE 13

8-Bromodihydrocodeinone hydrobromide

A suspension of thebaine (3.11 g) in methyl ethyl ketone (20 ml) was stirred at 18° C., and dry hydrogen bromide was bubbled in. A bulky white solid formed which slowly dissolved as bubbling continued. After 15 minutes the reaction mixture began to turn cloudy and the addition of gas was stopped (3.1 g HBr had been added). Stirring was continued for a further 45 minutes at 20° before cooling the reaction mixture to 5° C., and stirring for 10 minutes. The solid was filtered off, washed with cold methyl ethyl ketone (2 × 3 ml) and dried in a vacuum oven to give the title compound (2.82 g), identified by its IR spectrum.

EXAMPLE 14

8-Bromodihydrocodeinone hydrobromide

Anhydrous hydrogen bromide (7.95 g) was bubbled into a chilled (−15° C.) suspension of thebaine (3.11 g) in methyl isopropyl ketone (25 ml) over a total period of one hour ten minutes. (Cooling bath removed after first ten minutes). The solid dissolved slowly and almost immediately a fine precipitate began to separate. When the addition was complete the cooling bath (−10° to −15° C.) was replaced and stirring continued for 2 hours.

The product was filtered off, washed with a small volume of cold methanol and dried in vacuo to give the title compound (2.26 g), m.p. 193°–195° C. The structure was confirmed by IR spectroscopy and TLC (one spot).

EXAMPLE 15

8-Bromodihydrocodeinone hydrobromide

A solution of thebaine (3.11 g) in chloroform (50 ml) was dried by azeotropic distillation (14 ml chloroform removed). Cold, acetophenone (5 g) was then added and the flask further cooled in an ice-bath. Anhydrous hydrogen bromide (3.92 g) was introduced into the solution with vigorous stirring over a period of 10 minutes. Half an hour later the cooling bath was removed. Almost immediately a fine solid began to separate. The product was filtered off two hours later, washed with chloroform and dried in vacuo to give the title compound (3.74 g), m.p. 191°–193° C. The structure was confirmed by IR spectroscopy and TLC.

EXAMPLE 16

8-Bromodihydrocodeinone hydrobromide

An azeotropically dehydrated solution of thebaine (3.11 g) in chloroform (50 ml reduced to 35 ml) was cooled in an ice-bath and treated with methyl benzyl ketone (5.0 g). With vigorous magnetic stirring, dry hydrogen bromide gas (3.72 g) was introduced into the solution over a period of 7 minutes. The ice-bath was removed after ten minutes and eight minutes later a precipitate began to separate. Stirring was continued for a further two hours when the product was filtered off, washed with chloroform and dried in a vacuum oven to give the title compound (3.64 g), m.p. 179°–181° C. The IR spectrum and TLC were consistent with the structure assigned.

EXAMPLE 17

8-Bromodihydrocodeinone hydrobromide

A solution of thebaine (3.11 g) in chloroform (50 ml) was dried by azeotropic distillation (15 ml chloroform removed) and cooled in an ice-bath to 1° C. Ethyl acetoacetate (5.1 g) was added and dry hydrogen bromide (3.73 g) bubbled into the solution with magnetic stirring over a period of six minutes. Twelve minutes later the reaction mixture became cloudy and solid began to separate. After ten minutes the cooling bath was removed. Stirring was continued for a further two hours when the solid was collected by filtration, washed with chloroform and dried in vacuo overnight to give the title compound (3.44 g), m.p. 187°–189° C., characterised by its IR spectrum and TLC.

EXAMPLE 18

8-Bromodihydrocodeinone hydrobromide

A solution of thebaine (3.11 g) in chloroform (35 ml) containing chloral hydrate (1.82 g) was cooled in an ice-bath. Dry hydrogen bromide was bubbled into the solution over a period of 8 minutes with stirring to give an orange solution. The cold bath was removed after 30 minutes and after a further 20 minutes the reaction mixture was refrigerated for two days when it was found that a solid had been deposited. This product was filtered off, washed with chloroform and dried in vacuo to give the title compound (1.96 g), m.p. 173°–178° C., characterised by its IR spectrum and TLC.

EXAMPLE 19

8-Bromodihydrocodeinone hydrobromide

A solution of thebaine (3.11 g) and benzophenone (3.64 g) in azeotropically dried chloroform (50 ml) was cooled to 3° C., and anhydrous hydrogen bromide gas (4.62 g) bubbled in with stirring over 17 minutes. Stirring was continued for a further 2¾ hours during which time a fine solid separated. The solid was collected, washed with chloroform and dried in vacuo to give the title compound (3.25 g), m.p. 179°–181° C., the structure of which was confirmed by IR spectrum and TLC.

EXAMPLE 20

8-Bromodihydrocodeinone hydrobromide

A solution of thebaine (3.11 g) and butane-2,3-dione (4 ml; 3.92 g) in dried chloroform (35 ml) was cooled in an ice bath. Dry hydrogen bromide gas (3.72 g) was bubbled in with stirring. After an hour a considerable precipitate had formed. Methanol (10 ml) was added and the mixture stored in the refrigerator over a weekend. The solid was collected, washed with methanol and dried in vacuo to give the title compound (3.22 g), m.p. 197°–199° C., characterised by IR spectrum and TLC.

EXAMPLE 21

8Chlorodihydrocodeinone hydrochloride

A cold (−10° C.) solution of thebaine (2 g) in chloroform (6 ml) was treated portionwise with stirring with a solution of hydrogen chloride (1.36 g) in acetic acid (8 ml) over a 5 minute period. The colour of the solution gradually changed from buff to orange brown on stirring and a fine solid separated slowly. After stirring for 1½ hours the solid was collected, washed with chloroform and dried in vacuo at 30° C. to give the title compound (1.06 g), m.p. 209°–211° C., characterised by its infra red spectrum.

EXAMPLE 22

8-Chlorodihydrocodeinone hydrochloride

A suspension of thebaine (3.89 g) in acetone (50 ml) was chilled (−15″ C.) and anhydrous hydrogen chloride bubbled in with magnetic stirring. The solid dissolved after 4 minutes to give an orange solution. A total of 5.6 g hydrogen chloride was added. The mixture was stirred for 7 minutes when nitrogen was slowly bubbled in to remove some of the excess hydrogen chloride. The solution became cloudy and a fine precipitate began to separate. The nitrogen bubbling was stopped. Stirring was continued for 45 minutes when the solid was collected, washed with a small volume of acetone and dried to in vacuo to give the title compound (2.18 g), m.p. 208°–210° C. (dec.), characterised by its infra-red spectrum.

EXAMPLE 23

8-Iododihydrocodeinone hydroiodide

A suspension of thebaine (3.11 g) in acetone (50 ml) was treated with potassium iodide (7.5 g) and p-toluene sulphonic acid hydrate (8.64 g) with stirring at room temperature. A thick precipitate of potassium p-toluene sulphonate separated. After one hour forty minutes the solid was filtered off. On standing at room temperature a second solid crystallised which was found to be different from the first. This was collected, washed with acetone and dried to give the title compound (240 mg) m.p. 214°–218° C., IR(KBr disc) 2600 cm$^{-1}$: quaternary N-H; 1725 cm$^{-1}$: nonconjugated 6-ring ketone.

A sample (50 mg) of the product was treated with dilute ammonium hydroxide. The mixture was extracted with chloroform and the extract examined by TLC. The single spot was identified as codeinone.

EXAMPLE 24

Codeinone

A suspension of 8-bromodihydrocodeinone hydrobromide (459 mg) in water (5 ml) was treated dropwise, with cooling (ice bath) and magnetic stirring, with 1N sodium hydroxide solution (1.8 ml) to pH 10. The addition took place over 5 minutes and stirring was continued for a further 25 minutes when the solid was filtered off, washed thoroughly with water and dried in a vacuum oven to give the title compound (160 mg), m.p. 170°–175° C. The structure was confirmed by IR spectroscopy and TLC (one spot).

EXAMPLE 25

Codeinone

Anhydrous hydrogen bromide in glacial acetic acid (6 ml of 45% w/v solution) was added dropwise with stirring to a cooled (−15° C.) solution of thebaine (2 g) in chloroform (6 ml) over a period of 9 minutes. When the addition was complete the Drikold bath was removed and the temperature allowed to rise.

A fine buff solid separated from the dark brown solution. After a total of 45 minutes the entire mixture was transferred to a dropping funnel and added slowly to a stirred mixture of sodium bicarbonate (15.9 g), water (30 ml) and crushed ice (100 g). The addition took place over a period of 10 minutes and stirring was continued for a further 30 minutes. The mixture was filtered to remove unreacted sodium bicarbonate and the solid thoroughly washed with chloroform (40 ml). The aqueous phase was removed and extracted with fresh chloroform (50 ml then 20 ml). The combined extracts were washed with brine, dried over $Na_2SO_4$ and evaporated under reduced pressure. The residue (3.06 g) was found to be a salt of codeinone. The solid was redissolved in chloroform (20 ml) and shaken with 2N ammonium hydroxide solution. The chloroform layer was separated, washed with brine, dried over $Na_2SO_4$, and evaporated under reduced pressure. A solid crystallised which was dried to give the title compound (1.88 g), m.p. 156°–158° C. The infra red spectrum and TLC, which showed only traces of other impurities, confirmed the structure assigned.

EXAMPLE 26

Codeinone

Triethylamine (220 mg) was added to a stirred, chilled (5° C.) suspension of 8-bromodihydrocodeinone hydrobromide (459 mg) in water (15 ml). The mixture was stirred for 30 minutes. The solid was filtered off, washed with water and dried in vacuo to give the title compound (260 mg), m.p. 167°–169° C., identified by infra red spectrum and TLC.

EXAMPLE 27

Codeinone

A mixture of 8-bromodihydrocodeinone hydrobromide (495 mg), dimethyl sulphoxide (5 ml) and propylene oxide (10 ml) was heated at 35° C. for two hours when it was poured into cold water (100 ml) and extracted with chloroform (3 × 25 ml). The combined extracts were dried ($Na_2SO_4$) and evaporated to leave a gum. On trituration with methanol the gum crystallised. The colourless crystals were collected, washed with a few drops of methanol and dried to give the title compound (160 mg), m.p. 186°–187° C. The infra-red spectrum was identical to that of an authentic sample of codeinone.

EXAMPLE 28

Codeinone from 8-chlorodihydrocodeinone hydrochloride

A suspension of 8-chlorodihydrocodeinone hydrochloride (370 mg) in a mixture of water (10 ml) and methanol (2 ml) was treated dropwise with stirring over 3 minutes with 2N sodium carbonate solution (2 ml). The solid dissolved and after stirring for 10 minutes a crystalline solid precipitated. This was filtered off, washed with water and dried in vacuo to give the title compound (250 mg), characterised by its infra red spectrum and by TLC.

EXAMPLE 29

Codeinone

A solution of sodium ethoxide (680 mg) in ethanol (40 ml) was cooled in an ice bath and treated portionwise with stirring with 8-bromodihydrocodeinone hydrobromide (2.3 g). When the addition was complete stirring was continued for a further 20 minutes. A fine while solid remained in a pale yellow solution.

The solid was filtered off and the ethanol removed under reduced pressure. The residue was extracted with ethyl acetate (40 ml). Evaporation of the ethyl acetate yielded crystals of the title compound (1.3 g), characterised by TLC and IR spectrum.

EXAMPLE 30

Codeinone

A suspension of 8-bromodihydrocodeinone (2.3 g) in water (30 ml) was cooled (below 10° C.) in a cold water bath and treated dropwise with stirring with an aqueous solution of tetramethylammonium hydroxide (3.5 ml; ca. 25% of w/v). The pH was not allowed to exceed 10 throughout the 25 minute addition time. Stirring was continued for 15 minutes after the addition was complete.

A creamy solid remained in a pale green solution. The solid was filtered off, washed with water and dried in vacuo to give the title compound (1.2 g), characterised by TLC (one spot) and IR spectrum.

EXAMPLE 31

Codeine

Sodium borohydride (80 mg) was added to a chilled (10° C.) solution of methanol (7 ml) in N sodium hydroxide solution (5 ml). Keeping the temperature below 10° C. by means of an ice bath, 8-bromodihydrocodeinone hydrobromide (918 mg) was added portionwise with stirring over a period of 15 minutes. The resultant pale yellow solution was stirred for an hour and filtered to remove some insoluble matter. Chloroform (25 ml) and water (30 ml) were added and the mixture shaken. The layers were separated and the chloroform layer washed free of alkali with brine, dried ($Na_2SO_4$) and evaporated under reduced pressure. The residue (650 mg) displayed 4 spots on TLC. The major spot corresponded to codeine. This was confirmed by GLC where the major peak had the correct retention time for codeine.

EXAMPLE 32

Codeine

Thebaine (2.0 g) was dissolved in warm glacial acetic acid (10 ml) then chilled in an ice/water bath. A 45% w/v solution of anhydrous hydrogen bromide in glacial acetic acid (6 ml, 2.7 g HBr) was added dropwise with stirring over 9 minutes. Stirring was continued for 20 minutes during which time a fine precipitate separated. Methanol (75 ml) was added to a solution of sodium hydroxide (12.72 g) in water (75 ml). This solution was chilled (10° C.) and sodium borohydride (247 mg) added. The above slurry of 8-bromodihydrocodeinone hydrobromide in acetic acid was added portionwise to the sodium hydroxide-sodium borohydride mixture with vigorous stirring over 34 minutes keeping the temperature below 10° C. by means of an ice bath. After the addition, the mixture was allowed to stir for 30 minutes. Chloroform (50 ml) was added, the mixture stirred vigorously, allowed to settle and the layers separated. The aqueous phase was extracted with fresh chloroform (2 × 20 ml). The combined chloroform extracts were washed with brine (3 × 50 ml), dried ($Na_2SO_4$) and evaporated under reduced pressure. Final traces of solvent were removed under high vacuum. The fluffy off-white solid (1.85 g) displayed one major spot on TLC and one major peak on GLC, both of which corresponded to codeine. Codeinone was absent, and only minor amounts of other alkaloidal substances were present.

EXAMPLE 33

Codeine

A solution of thebaine (6.22 g) in glacial acetic acid (20 ml) was stirred at 15° C., and treated dropwise over 5 minutes with a 45% w/v solution of hydrogen bromide in glacial acetic adid (12.6 ml, 3.5 equivalents). TLC examination of a sample withdrawn 15 minutes after completion of the addition showed that the reaction was complete. The reaction mixture was then added slowly to a stirred slurry of sodium carbonate (62.5 g) in water (150 ml) keeping the temperature below 5° C. Methanol (250 ml) and water (100 ml) were added and the crude codeinone was reduced by portionwise addition of sodium borohydride (0.76 g) with stirring at 20° C. A sample was taken after 16 hours and the reduction was found to be complete (TLC). The reaction mixture was then filtered to remove inorganic solids and the filtrate was concentrated under reduced pressure until most of the methanol had been removed. The residual solid in the filter was washed with chloroform (100 ml) and the chloroform wash was used in two equal portions to extract the above aqueous concentrate. The chloroform extract was washed with water (25 ml), dried over sodium sulphate and the solvent removed under reduced pressure to give the title compound (3.88 g) identical by TLC and GLC with an authentic sample.

EXAMPLE 34

Codeine

A solution of anhydrous hydrogen bromide (2.92 g) in acetic acid (6.5 ml) was added dropwise with stirring to a cooled (iced water bath) solution of thebaine (3.11 g) in acetic acid (12 ml) over a period of 5 minutes. The resultant dark red solution formed a precipitate of 8-bromodihydrocodeinone hydrobromide after 5 minutes. The iced water bath was removed and stirring continued for a further 50 minutes. Piperidine (27 g) was dissolved in a mixture of water (50 ml) and methanol (50 ml) and cooled to 0° C. Sodium borohydride (370 mg) was added to this solution with stirring. The slurry of 8-bromodihydrocodeinone hydrobromide was added dropwise with vigorous stirring to the piperidine/sodium borohydride solution over 10 minutes while maintaining the temperature below 0° C. The cooling bath was removed and stirring continued for a further 25 minutes. The reaction mixture was extracted with chloroform (3 × 50 ml) and the combined chloroform extracts washed with water, dried ($Na_2SO_4$) and evaporated to leave an oil. Examination of the latter by TLC and GLC showed that codeine was the principal product present.

EXAMPLE 35

Codeine

A cold (−10° C.) solution of anhydrous hydrogen chloride (1.1 g) in acetic acid (9 ml) was added portionwise to a cold (−10° C.) solution of thebaine (2 g) in chloroform (8 ml) with stirring. The addition took place over 2 minutes and when complete the cooling bath was removed. After stirring for 1½ hours 8-chlorodihydrocodeinone hydrochloride separated out. Stirring was continued for a further 45 minutes. A solution of sodium hydroxide (7.5 g) in a mixture of water (50 ml) and methanol (50 ml) was prepared and chilled. Sodium borohydride (236 mg) was added to this solution.

The suspension of 8-chlorodihydrocodeinone hydrochloride in the above reaction mixture was added slowly with vigorous stirring to the solution of sodium hydroxide/sodium borohydride in aqueous methanol keeping the temperature below 0° C. After stirring for 30 minutes, the reaction mixture was extracted with chloroform (4 × 30 ml) and the combined extracts were washed with brine until neutral, dried ($Na_2SO_4$) and evaporated under reduced pressure. The product was dried to give the title compound (1.78 g), characterized by TLC and GLC. A recrystallised sample melted at 153–156° C., and gave an infra red spectrum identical to that of an authentic sample of codeine.

EXAMPLE 36

Codeine

A slurry of thebaine (31.1 g) in a mixture of chloroform (100 ml) and methyl ethyl ketone (100 ml) at 5° was treated with anhydrous hydrogen chloride. The solid slowly dissolved to give a clear yellow solution after 26.34 g of hydrogen chloride had been added. The reaction, however, was incomplete and more hydrogen chloride was bubbled in. A total amount of 36.27 g of hydrogen chloride was added over a two hour period. The addition of water (200 ml) to the mixture gave a creamy slurry. Sodium hydroxide (40 g) in water (200 ml) was added slowly at 15° C. to give an emulsion. The mixture was filtered and the phases separated. The filter paper was washed with chloroform (2 × 150 ml + 3 × 100 ml) before using the washings to extract the aqueous phase. The combined chloroform extracts were washed with N sulphuric acid (3 × 100 ml). (Some crystallizing of codeinone sulphate took place). Methanol (300 ml) was added to give a clear brown solution which was cooled to 15° C., and basified with 2N sodium hydroxide (150 ml). After filtering to remove some insoluble solid, the solution was treated portionwise with sodium borohydride (3.8 g). The mixture was stirred overnight at room temperature. The crude codeine was extracted out with chloroform (1 × 200 ml + 4 × 150 ml). The combined extracts were dried ($Na_2SO_4$) and evaporated to give a fluffy beige solid (30.44 g). This solid was dissolved in a mixture of ethanol (43 ml) and water (53 ml) and treated dropwise with stirring with a 1:1 mixture of concentrated sulphuric acid and water (5.75 ml). Codeine sulphate crystallized almost immediately. After refrigerating the product was collected, washed with ice-cold 1:1 aqueous ethanol (25 ml) and dried at 50° C. to give the title compound (23.25 g) as a colourless solid, characterised by IR and, after basification, by TLC and GLC.

EXAMPLE 37

Codeine

A two-necked flask containing 8-bromodihydrocodeinone hydrobromide (2.3 g), aluminium isopropoxide (3.06 g) and isopropanol (20 ml) was set up for distillation. A dropping funnel containing isopropanol was fitted in the second neck. After distilling slowly for 30 minutes (11 ml distillate; replaced by fresh isopropanol) it was found that acetone was present in the distillate. Half an hour later the second test for acetone was found to be negative. The reaction mixture was heated under reflux for an hour and then a further fraction distilled. This fraction also gave a negative test for acetone. The reaction mixture was cooled and poured into a mixture of water (150 ml) and isopropanol (15 ml). A brown, gelatinous solid formed. The mixture was stirred and Clarcel filter aid (ca 5 g) was added before filtering. The filter cake was washed carefully with chloroform (50 ml). The filtrate was extracted with chloroform (3 × 50 ml) and the combined chloroform extracts washed with brine, dried ($Na_2SO_4$) and evaporated to leave a gum (150 mg). The pH of the filtrate was adjusted to 11 with ammonia and the solution re-extracted with chloroform (4 × 30 ml). The combined extracts were washed with brine, dried ($Na_2SO_4$) and evaporated to leave a gummy solid (1.01 g). The two products were identical (by TLC) and were combined and triturated with benzene to give the title compound (600 mg) as buff crystals, m.p. 150–155° C., the identity of which was confirmed by IR spectrum, TLC and GLC.

EXAMPLE 38

Codeine

Anhydrous aluminium isopropoxide (3.06 g) and 8-chlorodihydrocodeinone hydrochloride (1.85 g) were suspended in isopropanol (20 ml) and heated until a slow distillation commenced. After three hours no more acetone appeared in the distillate and the reaction mixture was cooled, fresh isopropanol (10 ml) added and the mixture poured into water (100 ml). The mixture was filtered through a bed of kieselguhr and the filter cake basified with dilute ammonia and shaken with chloroform (50 ml). The solid was filtered off and washed with fresh chloroform (50 ml). The organic layer was separated, washed with brine, dried ($Na_2SO_4$) and evaporated to yield a fluffy solid (1.2 g). Trituration with benzene yielded crystals of the title compound (0.03 g), m.p. 149–154° C., characterised by its infra-red spectrum. GLC and TLC indicated the presence of a single compound with the correct retention time and Rf value for codeine.

EXAMPLE 39

Codeinone - In situ generation of hydrogen halide (a) A mixture of thebaine (3.11 g), oxalic acid dihydrate (2.52 g), sodium bromide (4.12 g) and acetone (30 ml) was stirred at room temperature. The reaction mixture was then heated under reflux for 3¼ hours, by which time the conversion was reasonably complete.

The acetone was distilled off under reduced pressure and the residue dissolved in water (25 ml) and filtered. Chloroform (50 ml) was added to the filtrate and the stirred mixture treated dropwise with 5N sodium hydroxide solution to pH 9. The chloroform layer was removed and the aqueous phase re-extracted with chloroform (2 × 30 ml). The combined chloroform extracts were washed with water until neutral, dried ($Na_2SO_4$) and the solvent removed under reduced pressure to give the title compound (1.98 g), identified by TLC and IR spectrum. (b) Thebaine (3.11 g) was dissolved in acetone (100 ml) on a steam bath. Whilst the solution was still warm powdered sodium bromide (6.18 g) and p-toluene sulphonic acid hydrate (11.4 g) were added with stirring. The mixture was heated under reflux for 45 minutes by which time all the thebaine had reacted. The sodium p-toluene sulphonate was filtered off, washed with acetone and the filtrate and washings stripped under reduced pressure to give a light brown oil. The oil was dissolved in water (20 ml), treated with chloroform (30 ml), cooled in an ice bath and basified, with vigorous stirring, to pH 9 with ammonia. The layers were separated and the aqueous phase extracted with fresh chloroform (2 × 50 ml). The combined extracts were washed with water, dried ($Na_2SO_4$) and evaporated to give the title compound (2.38 g) as a light brown solid. The structure was confirmed by TLC and IR spectroscopy of a recrystallised sample (m.p. 180–183° C.). (c) p-Toluene sulphonic acid monohydrate (8.64 g) was added to a suspension of thebaine (3.11 g) in acetone (75 ml). The solid dissolved and potassium chloride (3.36 g) was added to the solution. The mixture was heated under reflux for 30 minutes and then at 50° with magnetic stirring for a further two hours. The reaction mixture was cooled, filtered and evaporated to give a solid which was dissolved in water (20 ml). This solution was cooled in an ice bath and treated slowly with conc. ammonia to pH 9. The mixture was extracted with chloroform (3 × 40 ml) and the combined chloroform extracts dried ($Na_2SO_4$) and evaporated. The residue (1.24 g) crystallised on standing and was collected with the aid of a mixture (1:1) of acetone and ethyl acetate to give the title compound (850 mg), m.p. 177–180°, characterised by TLC and IR spectroscopy.

EXAMPLE 40

8-Bromodihydrocodeinone hydrobromide

A suspension of thebaine (3.11 g) in acetone (5 ml) was stirred with ice water bath cooling and treated dropwise over 5 minutes with a 45% w/v solution of hydrogen bromide in acetic acid (6.3 ml). By the end of the addition all the thebaine had dissolved and the product began to separate after a further 5 minutes. Examination by TLC of a reaction sample taken after 15 minutes showed that the reaction was complete.

The product was then filtered off, washed with cold acetone and dried in vacuo to give the title compound (2.63 g), m.p. 181–184° C.

We claim:

1. A process for the preparation of a compound of the formula

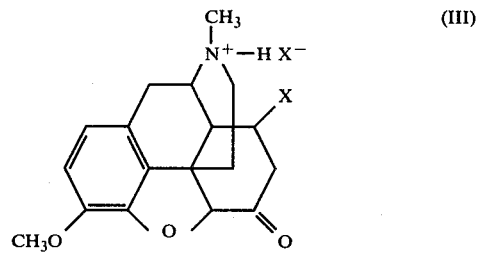

in which X represents a halogen atom, comprising reacting thebaine with a hydrohalic acid in the presence of a reactive compound selected from the group consisting of a lower aliphatic carboxylic acid, an enolizable carbonyl group-containing compound, chloral hydrate, water, benzaldehyde and benzophenone.

2. A process as claimed in claim 1 in which the reactive compound is a lower aliphatic carboxylic acid, an enolizable carbonyl group-containing compound, chloral hydrate or water.

3. A process as claimed in claim 1 in which the reactive compound is benzaldehyde or benzophenone.

4. A process as claimed in claim 2 in which the reactive compound is acetic acid.

5. A process as claimed in claim 1 in which the reaction is carried out under non-anhydrous conditions.

6. A process as claimed in claim 5 in which the reaction is carried out in the presence of up to 10% of water based on the overall volume of the reaction mixture.

7. A process as claimed in claim 1 in which the reaction is effected at a temperature between 10° C., and ambient.

8. A process as claimed in claim 1 in which the reactive compound is used in admixture with an inert solvent.

9. A process as claimed in claim 8 in which the inert solvent is a halogenated hydrocarbon or an ether.

10. A process as claimed in claim 1 in which a mixture of reactive compounds is used.

11. A process as claimed in claim 10 in which said mixture is aqueous acetic acid or an acetic acid/acetone mixture.

12. A process as claimed in claim 1 in which the reactive compound serves as the total solvent for the reaction.

13. A process as claimed in claim 1 in which the hydrohalic acid is generated in situ.

14. A process as claimed in claim 1 in which the reaction is carried out at a temperature of −20° C. to +80° C.

15. A process as claimed in claim 1 including isolating the desired compound of formula III.

16. A process for the preparation of codeine, comprising reacting thebaine with a hydrohalic acid in the presence of a reactive compound selected from the group consisting of a lower aliphatic carboxylic acid, an enolizable carbonyl group-containing compound, chloral hydrate, water, benzaldehyde or benzophenone to produce a compound of the formula

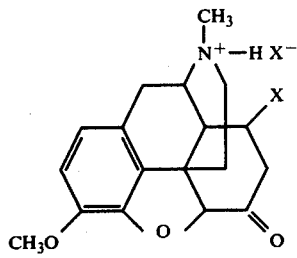 (III)

in which X represents halogen; treating said compound of formula III with a base to produce codeinone and reducing said codeinone without isolation of intermediate products.

17. A process for the preparation of codeine, comprising reacting thebaine with a hydrohalic acid in the presence of at least one reactive compound selected from the group consisting of a lower aliphatic carboxylic acid, an enolizable carbonyl group-containing compound, chloral hydrate, water, benzaldehyde and benzophenone and subsequently treating the resulting product with a mixture of a base and a reducing agent.

18. A process as claimed in claim 17 in which the base is sodium hydroxide and the reducing agent is sodium borohydride.

19. A process as claimed in claim 18 in which the sodium hydroxide and sodium borohydride are used in an alkanol.

20. A process for the preparation of codeine, comprising reacting thebaine with a hydrohalic acid in the presence of at least one reactive compound selected from the group consisting of a lower aliphatic carboxylic acid, an enolizable carbonyl group-containing compound, chloral hydrate, water, benzaldehyde or benzophenone and subsequently treating the resulting product with a reagent with basic properties capable of reducing a carbonyl group.

21. A process as claimed in claim 20 in which the basic reagent is aluminium isopropoxide.

22. A method for the preparation of codeine, comprising reacting a compound of the formula

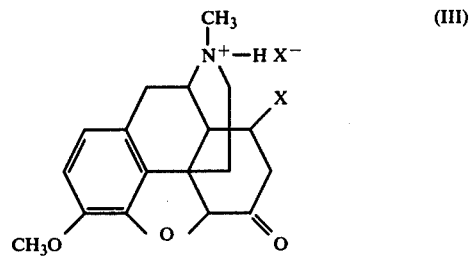 (III)

in which X represents a halogen atom with a mixture of a base and a reducing agent.

23. A process as claimed in claim 22 in which the base is sodium hydroxide and the reducing agent is sodium borohydride.

24. A process as claimed in claim 23 in which the sodium hydroxide and sodium borohydride are used in an alkanol.

25. A method for the preparation of codeine, comprising reacting a compound of the formula

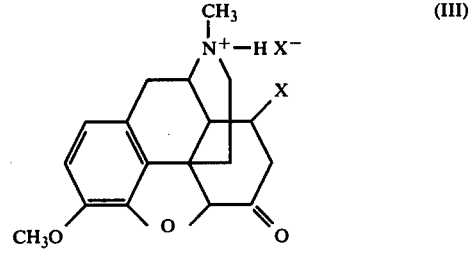 (III)

in which X represents a halogen atom with a reagent with basic properties capable of reducing a carbonyl group.

26. A process as claimed in claim 25 in which the basic reagent is aluminium isopropoxide.

* * * * *